(12) United States Patent
Ouchi

(10) Patent No.: US 6,719,752 B2
(45) Date of Patent: Apr. 13, 2004

(54) ENDOSCOPIC TREATMENT INSTRUMENT

(75) Inventor: Teruo Ouchi, Saitama (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 09/940,487

(22) Filed: Aug. 29, 2001

(65) Prior Publication Data

US 2002/0026178 A1 Feb. 28, 2002

(30) Foreign Application Priority Data

Aug. 31, 2000 (JP) ........................................ P2000-262228
Nov. 2, 2000 (JP) ........................................ P2000-335972

(51) Int. Cl.⁷ .......................... A61B 17/00; A61B 1/018
(52) U.S. Cl. .......................... 606/1; 600/104; 604/528
(58) Field of Search ........................ 606/1; 600/128, 600/139, 104, 106, 107; 604/264, 525, 528

(56) References Cited

U.S. PATENT DOCUMENTS

| 4,353,358 A | * | 10/1982 | Emerson ..................... 600/139 |
| 4,369,768 A | * | 1/1983 | Vukovic ..................... 600/123 |
| 4,601,713 A | * | 7/1986 | Fuqua ........................ 604/514 |
| 4,653,476 A | * | 3/1987 | Bonnet ....................... 600/106 |
| 4,742,817 A | * | 5/1988 | Kawashima et al. ......... 600/104 |
| 4,877,016 A | * | 10/1989 | Kantor et al. ............... 600/109 |
| 5,058,567 A | * | 10/1991 | Takahashi et al. .......... 600/139 |
| 5,271,381 A | * | 12/1993 | Ailinger et al. ............. 600/128 |
| 5,472,418 A | * | 12/1995 | Palestrant .................... 604/43 |
| 6,146,371 A | * | 11/2000 | DeWindt et al. ............ 604/506 |
| 2002/0082585 A1 | * | 6/2002 | Carroll et al. ............... 604/528 |

FOREIGN PATENT DOCUMENTS

| JP | 64-889 | 1/1989 |
| JP | 64-4335 | 2/1989 |
| JP | 1-15362 | 5/1989 |
| JP | 5-54348 | 8/1993 |
| JP | 6-1128 | 1/1994 |

* cited by examiner

*Primary Examiner*—John P. Leubecker
(74) *Attorney, Agent, or Firm*—Greenblum & Bernstein, P.L.C.

(57) ABSTRACT

In an endoscopic treatment instrument, a flexible tube has an area (A) which is to be located within an curved area (13) of an endoscope and which has a flattened cross-sectional shape.

12 Claims, 8 Drawing Sheets

ENDOSCOPIC TREATMENT INSTRUMENT

BACKGROUND OF THE INVENTION

The present invention relates to an endoscopic treatment instrument having a flexible tube which is to be inserted into or removed from a treatment instrument insertion channel in an endoscope.

Cannula tubes and papillotomy knives are treatment instruments of such a type that after being passed through a treatment instrument insertion channel in a duodenum fiberscope, their distal end is inserted into the bile or pancreatic duct for examination purposes. To use these treatment instruments, the direction in which the distal end portion projects beyond the endoscope must be subtly controlled so that it is suitable for insertion into the bile and pancreatic ducts.

Conventionally, as typically described in Examined Japanese Utility Model Publication (kokoku) No. 15362/1989, the need has been met by making the flexible tube predisposed to bend in arcuate form in the area of the treatment instrument which is to be located within the curved area of the endoscope in a use mode where said flexible tube is inserted into the treatment instrument insertion channel extending through the endoscope.

In a use mode, the bend-prone area of the flexible tube follows the curvature of the treatment instrument insertion channel in the curved area of the endoscope to regulate the directionality of its distal end portion.

A problem with this design is that the arcuate bend-prone area of the flexible tube often deforms as the flexible tube is passed from the entrance to the exit of the treatment instrument insertion channel and, as a result, the bend will either change direction or become less sharp.

If this occurs, the direction in which the distal end portion of the flexible tube projects beyond the endoscope during examination varies on each occasion, making it impossible for the doctor to insert the treatment instrument smoothly into the bile or pancreatic duct.

SUMMARY OF THE INVENTION

An object, therefore, of the invention is to provide such an endoscopic treatment instrument that the distal end portion of a flexible tube extending through the treatment insertion channel in an endoscope can be positively adjusted to project from the endoscope in a desired direction.

The endoscopic treatment instrument of the invention is characterized in that that part of a flexible tube which is to be located within a curved area of an endoscope in a use mode where the flexible tube is inserted into a treatment instrument insertion channel in an endoscope has a cross-sectional shape that promotes bending of that part of the flexible tube in a specified direction. With this design, the distal end portion of the flexible tube which has been passed through the treatment instrument insertion channel of the endoscope can be positively adjusted to project in a desired direction.

The present invention provides, as a preferred embodiment, an endoscopic treatment instrument having a flexible tube which is to be inserted into or removed from a treatment instrument insertion channel extending through the inserting section of an endoscope, said flexible tube being such that the part which is to be located within a curved area formed in the distal end portion of said inserting section in a use mode where said flexible tube is inserted into said treatment instrument insertion channel has a flattened or notched cross-sectional shape.

The flattened cross-sectional shape of the flexible tube may be elliptical or prolate. The notched cross-sectional shape may be formed by partially reducing the wall thickness of the flexible tube in a specified direction.

If desired, that part of the flexible tube which is to be located closer to the distal end than the part that is to be located within the curved area may be formed to have a flattened or notched cross-sectional shape which is twisted from the part to be located within the curved area.

A distal end treating member that is exposed on the outer surface of the flexible tube may be provided in that part of the flexible tube which is to be located closer to the distal end than the part to be located within the curved area.

An adjacent part of the flexible tube, which is closer to the distal end of the flexible tube than the part located within a curved area in the use mode may also have a flattened or notched cross-sectional shape.

The present disclosure relates to the subject matter contained in Japanese patent application Nos. 2000-262228 (filed on Aug. 31, 2000) and 2000-335972 (filed on Nov. 2, 2000), which are expressly incorporated herein by reference in their entireties.

DESCRIPTION OF THE PREFERRED EMBODIMENT

Embodiments of the invention are described below with reference to the accompanying drawings.

Figure 1:
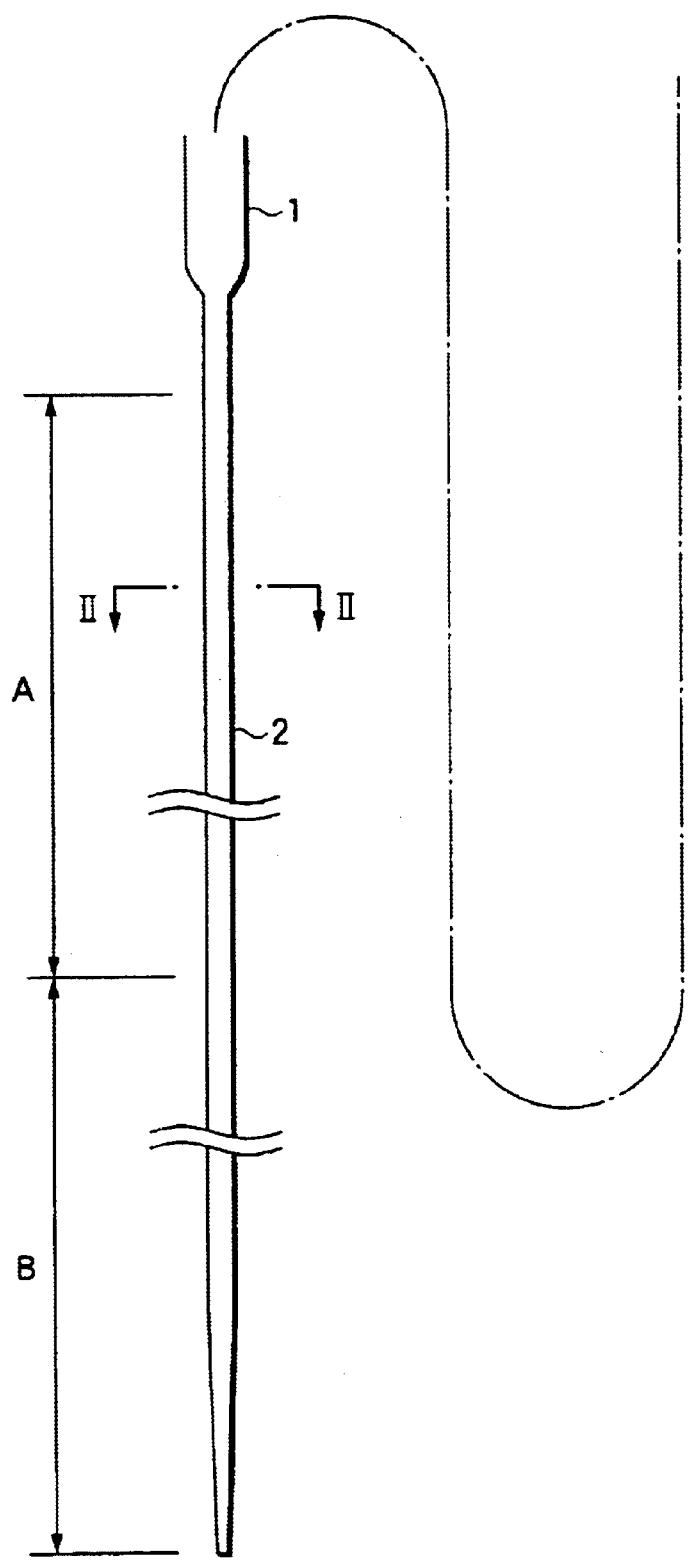
FIG. 1 is a side view showing the distal end portion of an endoscopic treatment instrument according to a first embodiment of the invention.

FIG. 1 shows the distal end portion of a cannula tube used to introduce a contrast medium into the bile or pancreatic duct through a treatment instrument insertion channel in a duodenum fiberscope.

The cannula tube is a flexible tube 1 having a contrast medium injection socket (not shown) connected at the basal end. The flexible tube 1 is typically made of a tetrafluoroethylene or polyethylene resin and measures about 2 mm in diameter and about 2 m in length.

To prevent buckling, a core rod may optionally be passed through the cannula tube. The flexible tube 1 is slightly tapered to be constricted in the distal end portion. The flexible tube 1 is hereunder referred to as the cannula tube 1.

Figure 4:
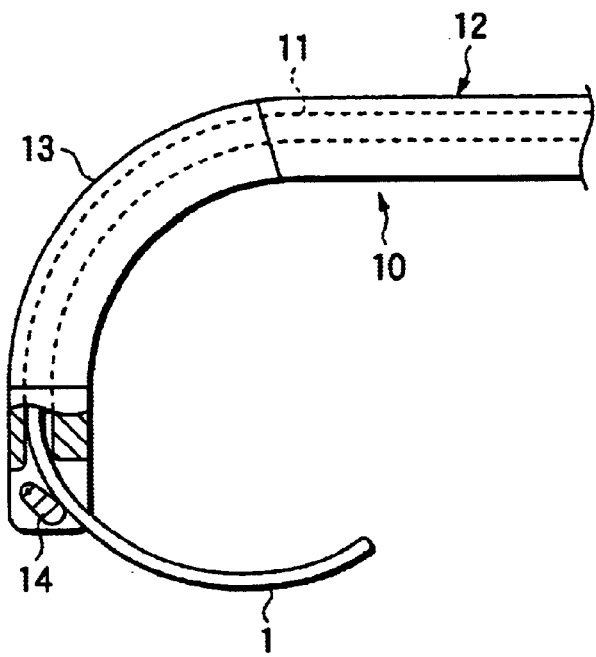
FIG. 4 is a side view of the endoscopic treatment instrument according to the first embodiment as it is in a use mode where its distal end portion is passed through an endoscope.

FIG. 4 shows the distal end portion of the cannula tube 1 in a use mode as it has been passed through a treatment instrument insertion channel 11 in a duodenum fiberscope 10.

The duodenum fiberscope 10 has an inserting section 12 in flexible tubular form which has an effective length of about 1.2 m. In the distal end portion of the inserting section 12, there is provided a curved area 13 which is freely bendable by remote control from a manipulating section (not shown) provided at the end of the fiberscope which is closer to the operator.

The treatment instrument insertion channel 11 is passed to extend through the entire length of the inserting section 12 and in its exit portion, there is provided a treatment instrument erecting mechanism 14 by which the projection of a treatment instrument passed through the channel 11 can be controlled to be directed either forward or backward.

When the cannula tube 1 is to be inserted into the bile or pancreatic duct, the curved area 13 bends in a specified direction (UP direction) as shown in FIG. 4 so that the projecting cannula tube 1 bends in almost the same direction as the curved area 13 bends.

Turning back to FIG. 1, the cross-sectional shape of the cannula tube 1 when taken in a section perpendicular to its longitudinal axis is a true circle throughout the range from its basal end to an area near the distal end portion. On the other hand, all the area A of the cannula tube 1 which is to be located within the curved area 13 in a use mode where the cannula tube 1 is passed through the treatment instrument insertion channel 11 in the duodenum fiberscope 10 and the area B which is closer to the distal end than the area A are flattened.

Figure 2:
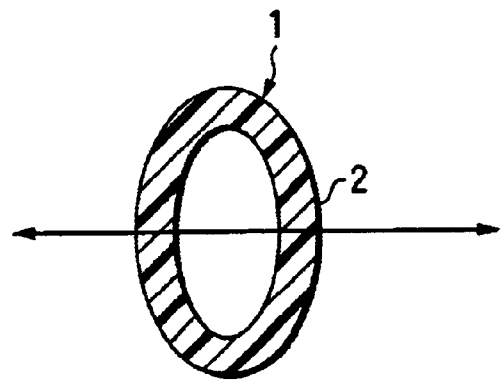
FIG. 2 is section II—II of FIG. 1.
Figure 3:
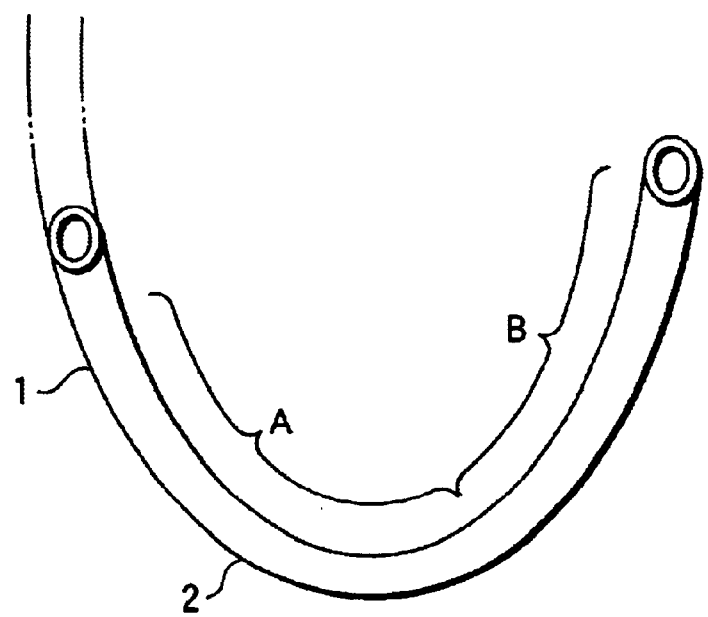
FIG. 3 is a partial perspective view of the endoscopic treatment instrument according to the first embodiment, with its distal end portion being bent.

As is clear from FIG. 2 which is section II—II of FIG. 1, the cannula tube 1 whose cross-sectional shape is a true circle in the area other than the areas A and B is pressed from both sides in the areas A and B to have a flattened shape such as an elliptical or prolate form (the flattened sides being indicated by 2 in FIG. 2).

With this design, the distal end portion of the cannula tube 1 acquires such propensity that a straight portion easily bends in only one direction where the flattened sides 2 face inward and outward but not in any other directions (that is, in the direction indicated by an arrow in FIG. 2). That is, the cross-sectional of the distal end portion of the cannula tube 1 promotes the bending of that portion of the flexible tube in a specified direction.

Therefore, as it passes through the curved area 13 of the treatment instrument insertion channel 11, the cannula tube 1 is spontaneously directed in a specified orientation so that its distal end portion can be positively adjusted to project in a desired direction from the distal end of the treatment instrument insertion channel 11.

Figure 5:
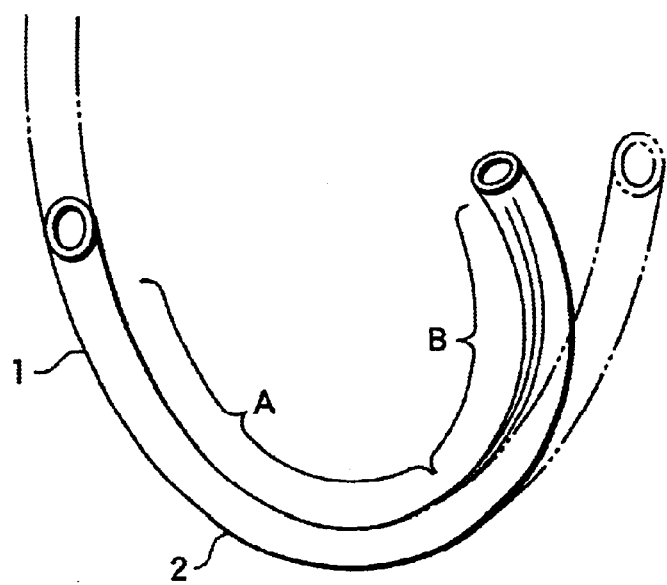
FIG. 5 is a partial perspective view of an endoscopic treatment instrument according to a second embodiment of the invention, with its distal end portion being bent.

FIG. 5 shows the distal end portion of the cannula tube 1 according to a second embodiment of the invention, in which said distal end portion is formed to have such a flattened cross-sectional shape that the flattened sides 2 are parallel to the longitudinal axis of the cannula tube 1 in the area A which is to be located within the curved area 13 but become gradually twisted in the area B which is closer to the distal end than the area A.

Figure 6:
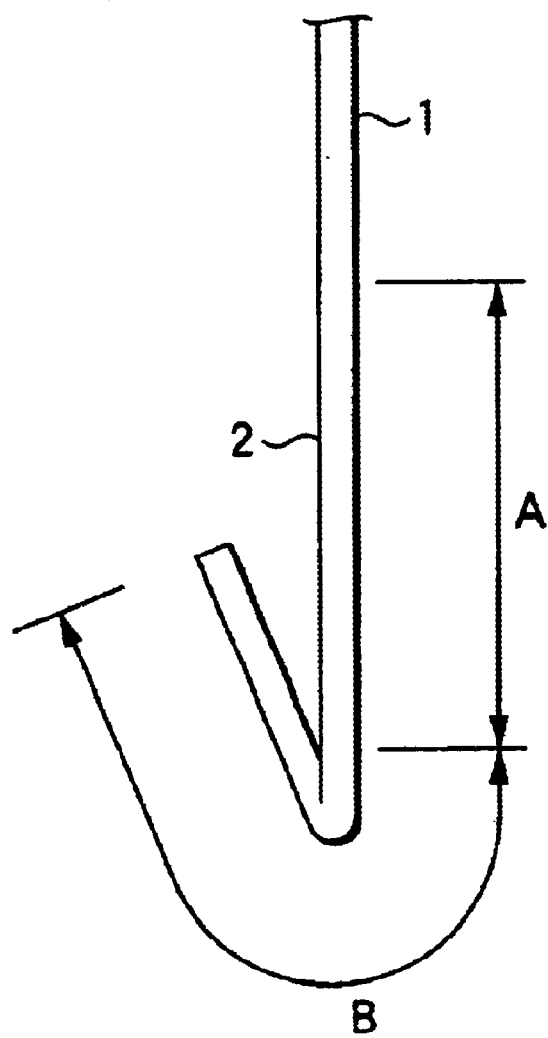
FIG. 6 is a sketch of the endoscopic treatment instrument according to the second embodiment, with its distal end portion being bent.

With this design, when the cannula tube 1 is bent at the distal end, the area B which is closer to the distal end than the area A which is to be located within the curved area 13 bends in a different plane than the area A, as shown in FIG. 6.

Therefore, by choosing an appropriate shape for the twist of the flattened sides 2, one can ensure that the distal end of the cannula tube 1 projects from the distal end of the inserting section 12 of the duodenum fiberscope 10 in any direction he likes.

Figure 7:
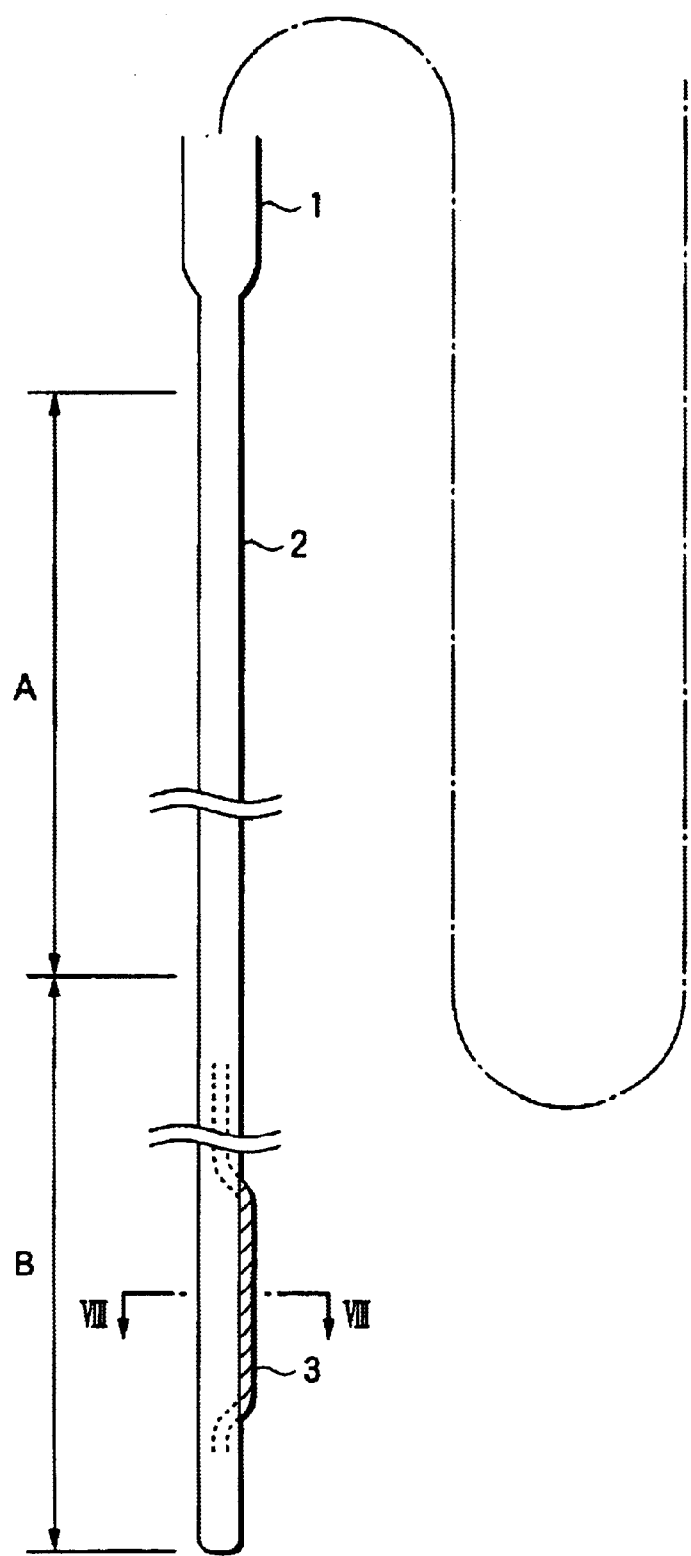
FIG. 7 is a side view showing the distal end portion of an endoscopic treatment instrument according to a third embodiment of the invention.

FIG. 7 shows the distal end portion of a papillotomy knife incorporating the concept of the invention. The flexible tube 1 has flattened sides 2 formed in the same way as in the first embodiment, except that an electrode wire 3 (distal end treating member) is exposed in the distal end portion of the flexible tube 1.

The electrode wire 3 is a conductor wire that is passed through the entire length of the flexible tube 1, except that it lies on the outer surface of the flexible tube 1 between a pair of holes made in the distal end portion of the flexible tube 1 and spaced apart along its longitudinal axis.

Figure 8:
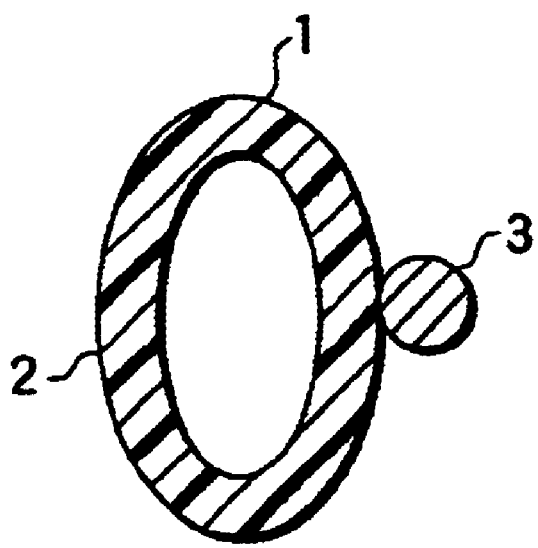
FIG. 8 is section VIII—VIII of FIG. 7.

As is clear from FIG. 8 which is section VIII—VIII of FIG. 7, if the electrode wire 3 is placed on either one of the flattened sides of the flexible tube 1, it can be located inside the curvature of the flexible tube 1 projecting from the duodenum fiberscope 10.

Thus, by proper adjustment of the position of the electrode wire 3 relative to the flattened sides 2, one can ensure that the electrode wire 3 has the desired positional relationship with the curvature of the flexible tube 1, whereby the electrode wire 3 can be situated in any direction he likes.

It should be noted that the cross-sectional shape of the flexible tube (cannula tube) 1 in the areas A and/or B is not limited to those described in connection with the first to third embodiment.

Figure 9:
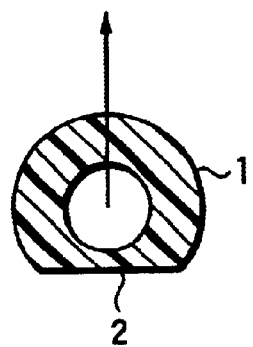
FIG. 9 is section II—II of FIG. 1 in a modified embodiment.

For example, a cross-sectional shape as shown in FIG. 9 may be employed.

That is, all the area A of the flexible tube 1 which is to be located within the curved area 13 in a use mode where the flexible tube 1 is passed through the treatment instrument insertion channel 11 in the duodenum fiberscope 10 and the area B which is closer to the distal end than the area A are so-shaped that the flexible tube 1 is partially reduced in thickness in a specified direction.

As is clear from FIG. 9 which corresponds to section II—II of FIG. 1, the outer part of the flexible tube 1 whose cross-sectional shape is a true circle in the area other than the areas A and B is notched in the specified direction (i.e. the outer part in the specified direction is notched) in the areas A and B to have such a notched shape that the wall thickness in the specified direction is reduced (the notched portion being indicated by 2 in FIG. 9).

Figure 12:
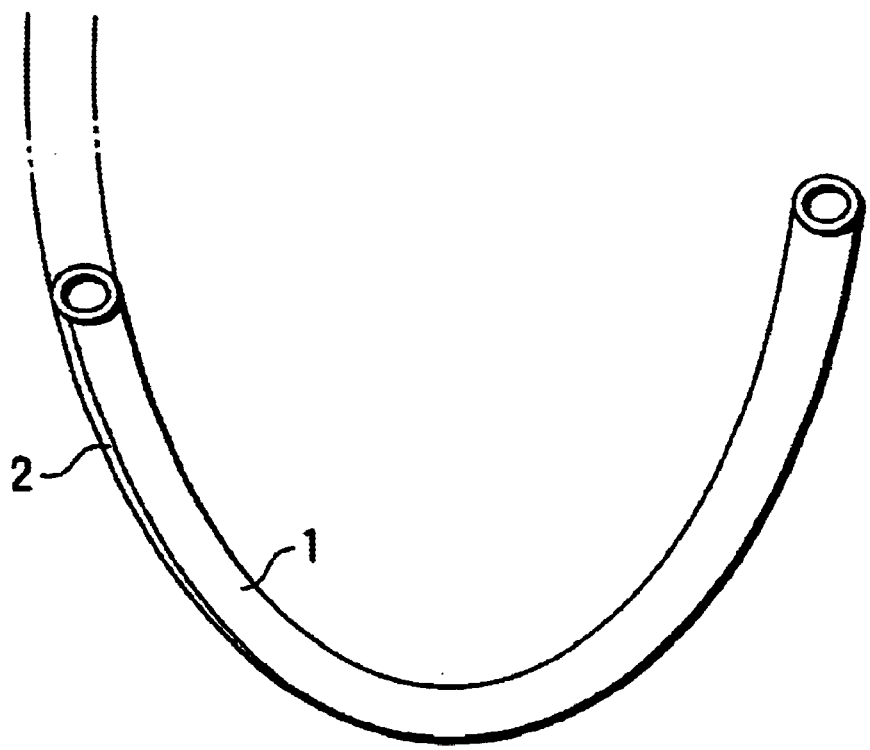
FIG. 12 is a partial perspective view of the endoscopic treatment instrument according to the modified embodiment, with its distal end portion being bent.

With this design, the distal end portion of the flexible tube 1 acquires such propensity that a straight portion easily bends in only one direction where the notched portion 2 is located radially outward in the curvature as shown in FIG. 12 but not in any other directions.

Therefore, as it passes through the curved area 13 of the treatment instrument insertion channel 11, the flexible tube 1 is spontaneously directed in a specified orientation so that its distal end portion can be positively adjusted to project in a desired direction from the distal end of the treatment instrument insertion channel 11.

Figure 10:
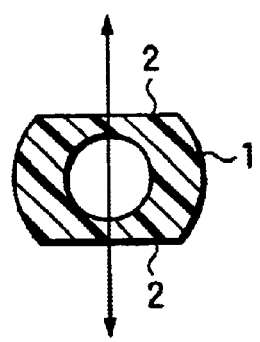
FIG. 10 is section II—II of FIG. 1 in another modified embodiment.

As shown in FIG. 10, another notched portion 2 may be added so that the notched portions 2 are located symmetrically at 180 degrees opposite positions with respect to the longitudinal axis of the flexible tube 1, thereby promoting the bending of the flexible tube 1 in the direction indicated by the arrow in FIG. 10.

Of course, the cross-sectional shapes exemplified as shown in FIGS. 9 and 10 may be employed in the second embodiment. The notched portion(s) 2 is parallel to the longitudinal axis of the flexible tube 1 in the area A which is to be located within the curved area 13 but become gradually twisted in the area B which is closer to the distal end than the area A.

With this design, when the flexible tube 1 is bent at the distal end, the area B which is closer to the distal end than the area A which is to be located within the curved area 13 bends in a different plane than the area A.

Therefore, by choosing an appropriate shape for the twist of the notched portion(s) 2, one can ensure that the distal end of the flexible tube 1 projects from the distal end of the inserting section 12 of the duodenum fiberscope 10 in any direction he likes.

Figure 11:
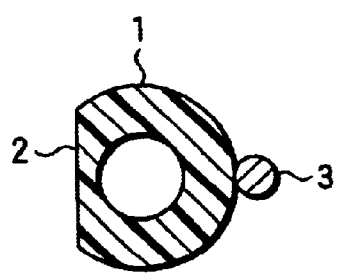
FIG. 11 is section VIII—VIII of FIG. 7 in yet another modified embodiment.

Also, the cross-sectional shapes exemplified as shown in FIGS. 9 and 10 may be employed in the third embodiment. FIG. 11 shows an example in which the cross-sectional shape shown in FIG. 9 is employed in the third embodiment.

As shown in FIG. 11 which corresponds to section VIII—VIII of FIG. 7, if the electrode wire 3 and the notched portions 2 are placed symmetrically at 180 degrees opposite positions with respect to the longitudinal axis of the flexible tube 1, the electrode wire 3 can be located inside the curvature of the flexible tube 1 projecting from the duodenum fiberscope 10.

Thus, by proper adjustment of the position of the electrode wire 3 relative to the notched portion 2, one can ensure that the electrode wire 3 has the desired positional relationship with the curvature of the flexible tube 1, whereby the electrode wire 3 can be situated in any direction he likes.

It should be noted that the present invention is by no means limited to the foregoing embodiments but can be applied to a wide range of treatment instruments that are passed through a treatment instrument insertion channel in endoscopes.

What is claimed is:

1. An endoscopic treatment instrument having a flexible tube provided in a treatment instrument insertion channel extending through an inserting section of an endoscope, said flexible tube being such that a portion thereof, located within a curved area formed in the distal end portion of said inserting section has a cross-sectional shape which promotes bending of said portion of the flexible tube in a first direction;

wherein a portion of said flexible tube located closer to the distal end than said portion located within said curved area has a cross-sectional shape that is formed to have a flattened or notched cross-sectional shape which is twisted from said portion located within said curved area.

2. The endoscopic treatment instrument according to claim 1, wherein the cross-sectional shape is a flattened cross-sectional shape.

3. The endoscopic treatment instrument according to claim 2, wherein the flattened cross-sectional shape is elliptical or prolate.

4. The endoscopic treatment instrument according to claim 1, wherein the cross-sectional shape is a notched cross-sectional shape.

5. The endoscopic treatment instrument according to claim 4, wherein the notched cross-sectional shape is formed by reducing a wall thickness of the flexible tube in a direction opposite from said first direction.

6. The endoscopic treatment instrument according to claim 1, wherein a portion of said flexible tube located closer to the distal end than said portion located within said curved area has a cross-sectional shape which promotes bending of said portion of said flexible tube located closer to the distal end in a second direction.

7. The endoscopic treatment instrument according to claim 1, wherein a distal end treating member that is exposed on an outer surface of said flexible tube is provided in a portion of said flexible tube located closer to the distal end than said portion located within said curved area.

8. An endoscopic treatment instrument for use with an endoscope, the instrument comprising:

a treatment instrument insertion channel extending through an inserting section of the endoscope, said treatment instrument insertion channel having a distal end and a curved area close to the distal end; and a flexible tube having a first area located within the curved area of said treatment instrument insertion channel, and a second area continuous with the first area and projecting from the distal end of said treatment instrument insertion channel, wherein the first area is more readily bendable in a first specified direction;

wherein the second area is more readily bendable in a second specified direction; and wherein the orientation of the second area is gradually changed so that said second specified direction at a distal end of the second area opposite from the first area is different from said first specified direction.

9. The endoscopic treatment instrument according to claim 8, wherein said first specified direction is identical to said second specified direction.

10. The endoscopic treatment instrument according to claim 8, wherein the first area has a notched cross-sectional shape.

11. The endoscopic treatment instrument according to claim 8, wherein a wall thickness of the first area is partially reduced to provide the ability to readily bend in a first specified direction.

12. The endoscopic treatment instrument according to claim 9, wherein the first area has an elliptical cross-sectional shape.

* * * * *